United States Patent
Sherman et al.

(10) Patent No.: US 7,329,282 B2
(45) Date of Patent: Feb. 12, 2008

(54) REVISION METHODS FOR A VERTEBRAL DEVICE

(75) Inventors: Michael C. Sherman, Memphis, TN (US); Lukas Eisermann, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 240 days.

(21) Appl. No.: 11/103,126

(22) Filed: Apr. 11, 2005

(65) Prior Publication Data

US 2006/0241632 A1  Oct. 26, 2006

(51) Int. Cl.
*A61F 2/44* (2006.01)
(52) U.S. Cl. ...................... 623/17.11; 606/61
(58) Field of Classification Search ............ 623/16.11, 623/17.11–17.16; 606/61
See application file for complete search history.

(56) References Cited

U.S. PATENT DOCUMENTS

| | | | |
|---|---|---|---|
| 4,702,236 A | 10/1987 | Tarabichy et al. | |
| 5,078,718 A | 1/1992 | Moll et al. | |
| 5,108,402 A | 4/1992 | Chin | |
| 5,147,403 A | 9/1992 | Gitelis | |
| 5,156,606 A | 10/1992 | Chin | |
| 6,273,891 B1* | 8/2001 | Masini | 606/91 |
| 6,479,565 B1 | 11/2002 | Stanley | |
| 6,852,095 B1 | 2/2005 | Ray | |
| 2004/0148028 A1 | 7/2004 | Ferree et al. | |
| 2004/0220296 A1 | 11/2004 | Lowman et al. | |
| 2004/0230307 A1 | 11/2004 | Eisermann | |
| 2004/0236424 A1 | 11/2004 | Berez et al. | |
| 2004/0243137 A1 | 12/2004 | Gorek | |
| 2005/0010304 A1 | 1/2005 | Jamali | |
| 2005/0043802 A1 | 2/2005 | Eisermann et al. | |
| 2005/0049623 A1 | 3/2005 | Moore et al. | |
| 2005/0049707 A1* | 3/2005 | Ferree | 623/17.13 |
| 2005/0055029 A1 | 3/2005 | Marik et al. | |
| 2005/0055098 A1* | 3/2005 | Zdeblick et al. | 623/17.11 |

* cited by examiner

*Primary Examiner*—Eduardo C. Robert
*Assistant Examiner*—Tara George
(74) *Attorney, Agent, or Firm*—Coats & Bennett, P.L.L.C.

(57) ABSTRACT

Embodiments of devices and methods for correcting a vertebral member and/or repositioning a vertebral device relative to the vertebral member. A vertebral device has been previously positioned relative to a vertebral member. Due to subsidence or other factors, the vertebral device has moved and is no longer in alignment. A positioning device is used for re-positioning the vertebral device. A delivery device is used for inserting a material to the vertebral member and/or vertebral device. The material is initially in a first state that is flowable to allow for insertion to the required location. The material changes to a second state that permanently fixes the position of the vertebral device relative to the vertebral member.

19 Claims, 5 Drawing Sheets

REVISION METHODS FOR A VERTEBRAL DEVICE

BACKGROUND

Vertebral devices are frequently inserted to vertebral members. These devices may partially or fully replace a problematic disc or vertebral member, support the vertebral member or other vertebral members, or provide movement between two or more vertebral members. Examples of intervertebral devices include Maverick, Prestige, and Bryan discs. Each of these vertebral devices is available from Medtronic Sofamor Danek, of Memphis Tennessee. The term "vertebral members" is used generally herein to refer to vertebrae that form the cervical, thoracic, lumbar, and sacral regions of the spinal column.

The vertebral devices are surgically attached to one or more vertebral members. Once mounted, the vertebral devices have an extended life and are reliable such that no further medical procedures are usually necessary. However, there are instances when it is necessary to surgically revise the vertebral devices. One instance is when one or more of the vertebral members become damaged causing the vertebral device to move and become improperly positioned. This may be caused by an osteopenia collapse or fracture resulting from a reduction in the normal content of the mineral calcium within the vertebral member. Other causes of a collapse or fracture may include the age of the patient, genetic factors, chronic diseases, or traumatic damage such as a fall or automobile accident. Another instance when surgical revision is necessary occurs if the vertebral device was not originally placed in the correct location relative to the vertebral member. In each instance, it is necessary to revise the vertebral device.

Previous revision methods have included removing the incorrectly positioned vertebral device from the patient. The surface of the vertebral member is then treated such as by removing the subsided bone, inserting new bone material into the fracture or void, and then re-mounting a new vertebral device. However, this previous method may require a more extensive and time consuming surgical procedure, result in an extended hospital stay for the patient, and not produce satisfactory results.

SUMMARY

The present invention is directed to embodiments of revising a vertebral device that has become misaligned relative to one or more vertebral members. One method may include accessing the vertebral device and the vertebral member. Once accessed, a positioning device may be used to contact the vertebral device and move it to a correct, properly aligned position. The positioning device may remain in contact and keep the vertebral device properly aligned as a delivery device is inserted into the subsided vertebral member. The material may be initially in a first state that may flow to fill the subsided space. The material may then change to a second state that is able to support the vertebral device in the proper position. Once properly supported, the positioning device may be removed.

DETAILED DESCRIPTION

Figure 1:
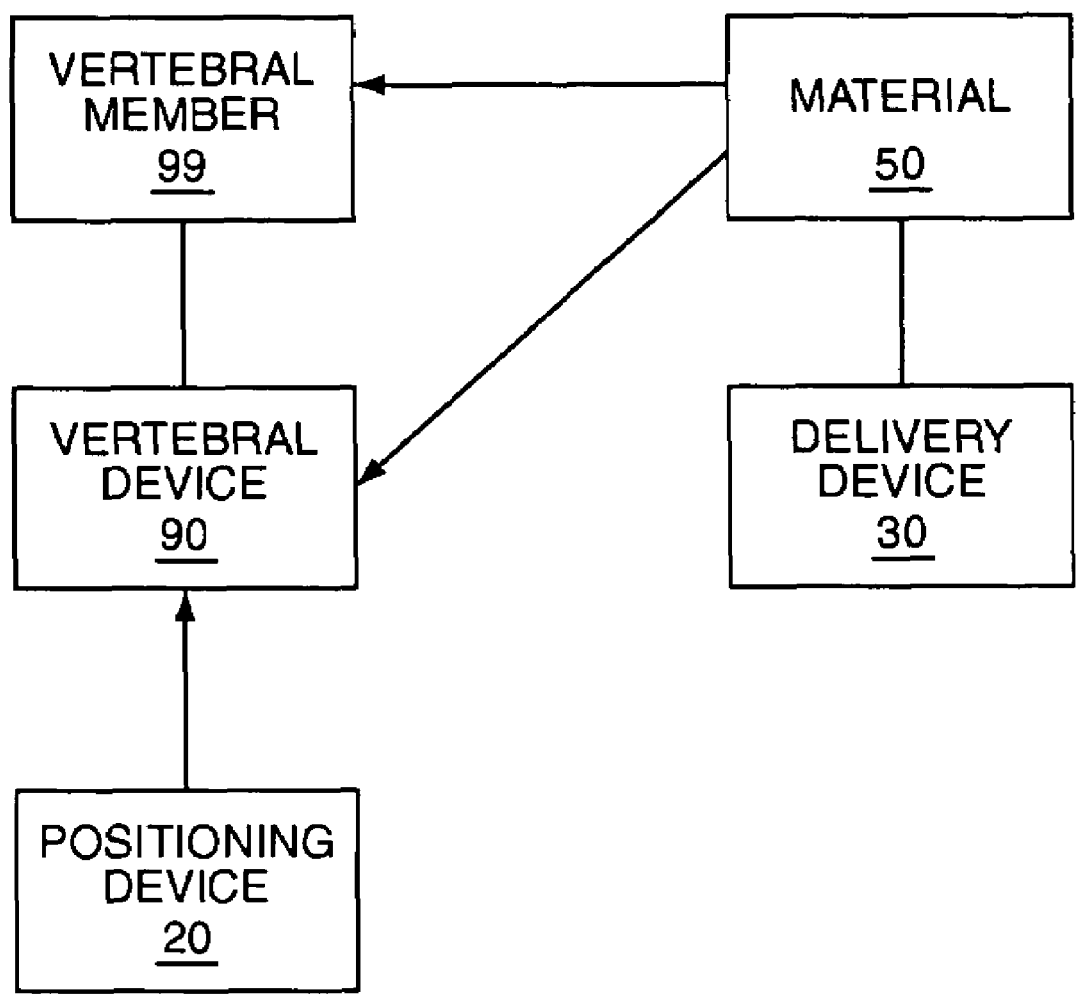
FIG. 1 is a schematic diagram of the elements of one embodiment of the present invention.

The present embodiments are directed to devices and methods for correcting a vertebral member and/or repositioning a vertebral device relative to the vertebral member. FIG. 1 schematically illustrates the elements associated with one embodiment. A vertebral device 90 has been previously positioned and attached to a vertebral member 99. Due to subsidence or other factors, the vertebral device 90 has moved and is no longer in alignment. A positioning device 20 re-positions the vertebral device 90. A delivery device 30 inserts a material 50 to the vertebral member 99 and/or vertebral device 90. The material 50 is initially in a first state that is flowable to allow for insertion to the required location. The material 50 changes to a second state that fixes the position of the vertebral device 90 relative to the vertebral member 99.

Figure 2:
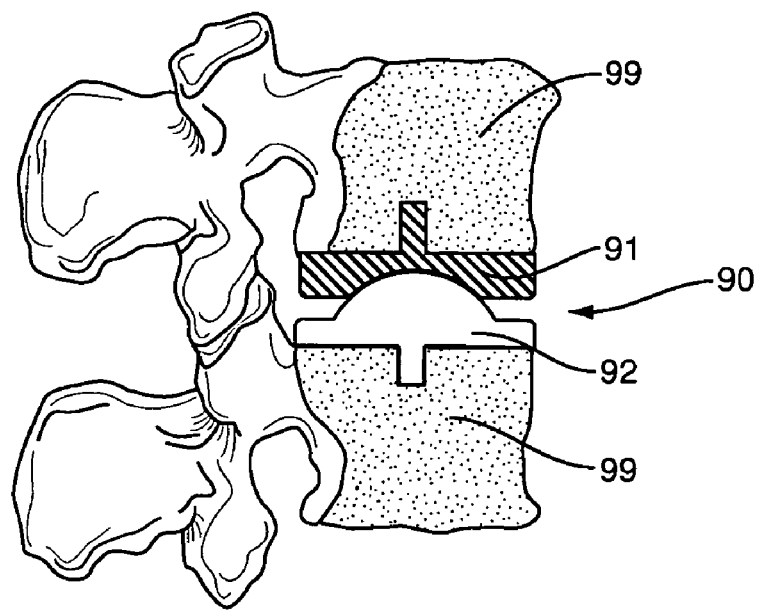
FIG. 2 illustrates a vertebral device mounted relative to vertebral members according to one embodiment of the present invention.
Figure 3:
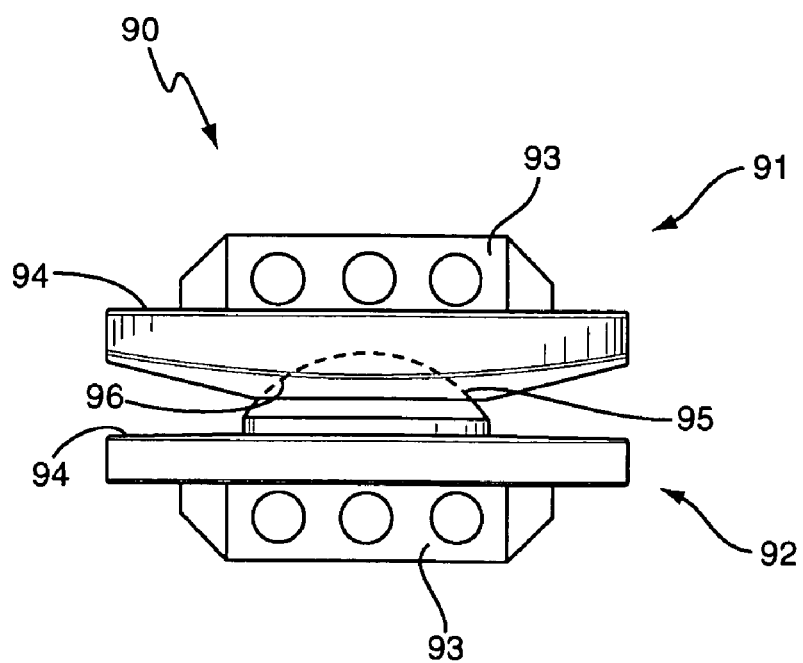
FIG. 3 illustrates a vertebral device according to one embodiment of the present invention.

FIGS. 2 and 3 illustrate one embodiment of a vertebral device 90. FIG. 2 illustrates the device 90 positioned between two adjacent vertebral members 99. In this embodiment, the vertebral device 90 is a disc replacement featuring a first section 91 mounted to a first vertebral member that compliments a second section 92 mounted to an adjacent vertebral member. Each section 91, 92 includes a mounting platform 94 that abuts against the end plate of the vertebral member 99, and a keel 93 that is mounted within a slot formed in the vertebral member 99. First member 91 includes a socket 96 sized to receive a complementary ball 95 of the second member 92. When properly mounted, the ball 95 seats within the socket 96 providing for relative movement between the adjacent vertebral members 99.

Figure 4:
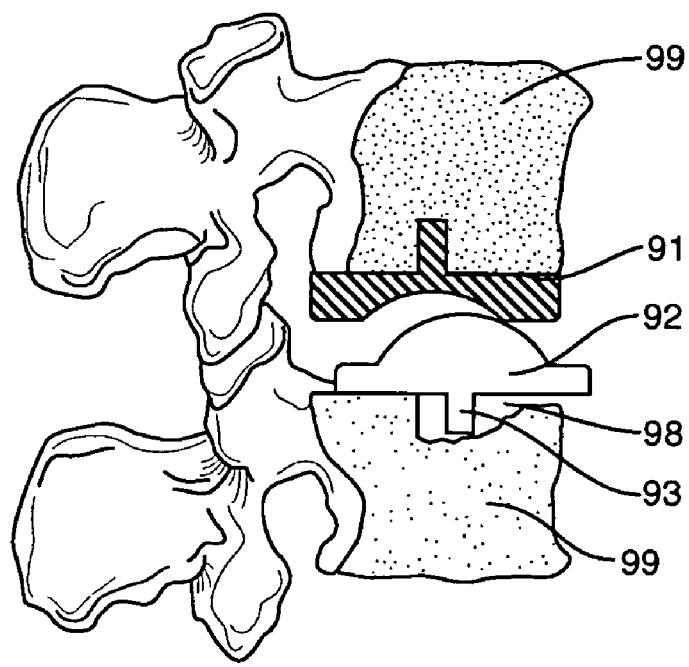
FIG. 4 illustrates a vertebral device being misaligned relative to the vertebral member according to one embodiment of the present invention.

In certain instances, the vertebral device 90 may become misaligned relative to the vertebral member 90. The misalignment occurs after the device 90 is inserted into the patient. FIG. 4 illustrates one example of the misalignment caused by subsidence in the vertebral member 99. A gap 98 caused by sinking or settling in the vertebral member 99 has formed below the second section 92. As a result, the second section 92 has become misaligned with the ball 95 no longer seating within the corresponding socket 96.

Figure 5:
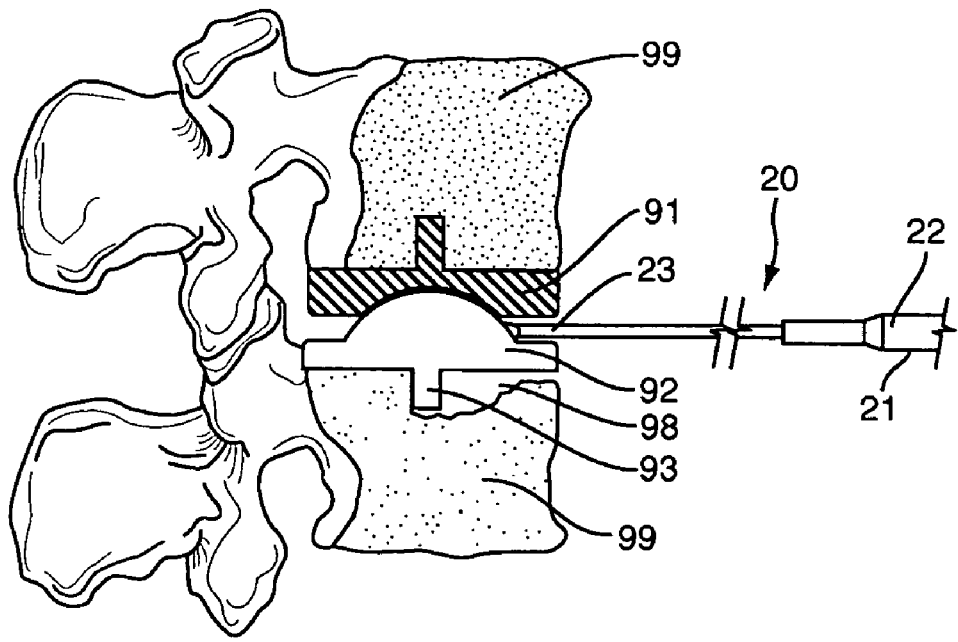
FIG. 5 illustrates a positioning device in contact with the vertebral device according to one embodiment of the present invention.

FIG. 5 illustrates one embodiment of a positioning device 20 used for contacting and repositioning the second section 92. The positioning device 20 has an elongated shape with a first end 21 and a second end 23. The elongated shape provides for the first end 21 to remaining spaced away from the vertebral member 99. In one embodiment, the device 20 has a length for the first end 21 to remain outside of the patient when the second end 23 is in contact with the vertebral device 90. The first end 21 may include a handle 22 for grasping and manipulating by the physician. The first end 21 may further include an adjustment mechanism (not illustrated) such as for adjusting or locking a size of the second end 23.

The second end 23 functions to contact the vertebral device 90. The second end 23 is configured to manipulate the vertebral device 90 and move it towards the correct alignment. The tip may also include a mount that can be mounted to the device. In one embodiment, the tip is threaded and can be mounted within a threaded opening in the device 90.

Figure 6:
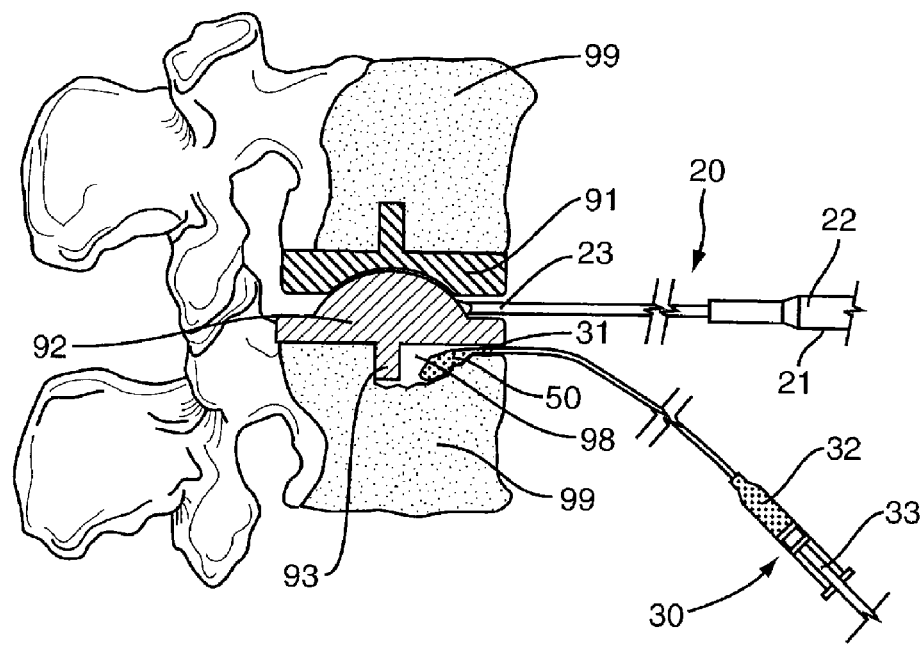
FIG. 6 illustrates a delivery device inserting a material into a gap formed between the vertebral member and the vertebral device according to one embodiment of the present invention.

While the alignment of the second section 92 is being held in proper position by the positioning device 20, a delivery device 30 inserts material 50 into the gap 98 as illustrated in FIG. 6. The delivery device 30 includes a reservoir 32 for holding a supply of material 50, and an actuator 33 for forcing the material from the reservoir 32 through a tip 31 and into the gap 98. In this embodiment, delivery device 30 is a syringe having a plunger that is squeezed to force the material through the tip 31. The tip 31 may be flexible to position it into the gap 98 from a variety of the angles and orientations.

Material 50 is inserted into the gap 98 while in a first flowable state. The first state may be a liquid or a semi-solid to allow the material 50 to move into and fill the gap 98. The flowable first state allows the tip 31 of the delivery device 30 to be positioned in a variety of gap locations. In the embodiment of FIG. 6, the tip 31 is placed at an edge of the gap 98 with the material 50 moving through and filling the gap 98. The tip 31 may also be positioned into the far reaches of the gap 98 and pulled slowly out of the gap 98 during material insertion as the material 50 fills the gap 98.

Figure 7:
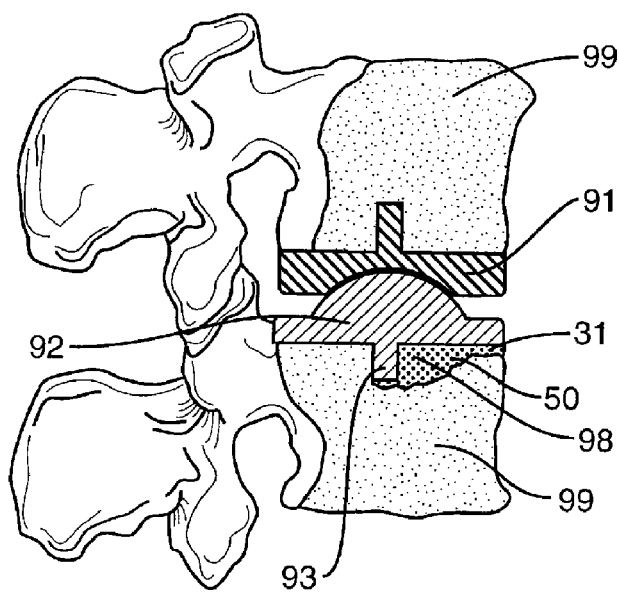
FIG. 7 illustrates the material in a second state that supports the vertebral device in proper alignment relative to one embodiment of the present invention.

After insertion, the material 50 changes to a second state that supports the vertebral device 90 in the corrected position. As illustrated in FIG. 7, the material 50 has changed to a second state allowing for removal of the positioning device 20. The material 50 in the second state may be is adequate to support the device 92 on the vertebral member 99 without any additional fasteners, such as screws. In one embodiment, the positioning device 20 remains in contact with the vertebral device 90 until the material 50 permanently sets in a final state. In another embodiment, the positioning device 20 may be removed from contact when the material 50 has cured to an intermediate state that is able to support the device 20, but prior to complete curing to the final second state.

The material 50 may include bone cements and specific organic bone mimicking compounds such as poly methy methacrylate (PMMA), calcium phosphate cement, or D.B.M. putty. One embodiment of the material 50 features an expanding bone cement. This expanding material 50 is placed into the gap 98 in the first state and flows through the gap 98. As it changes into the second state, the material 50 expands to fill the entirety of the gap 98. The positioning device 20 remains in contact with the device 92 as the material expands to maintain the position. If the positioning device 20 was removed, the expanding material 50 may force the material 50 from the correct alignment. One embodiment of an expanding cement is Kryptonite available from Doctor's Research Group.

Figure 8:
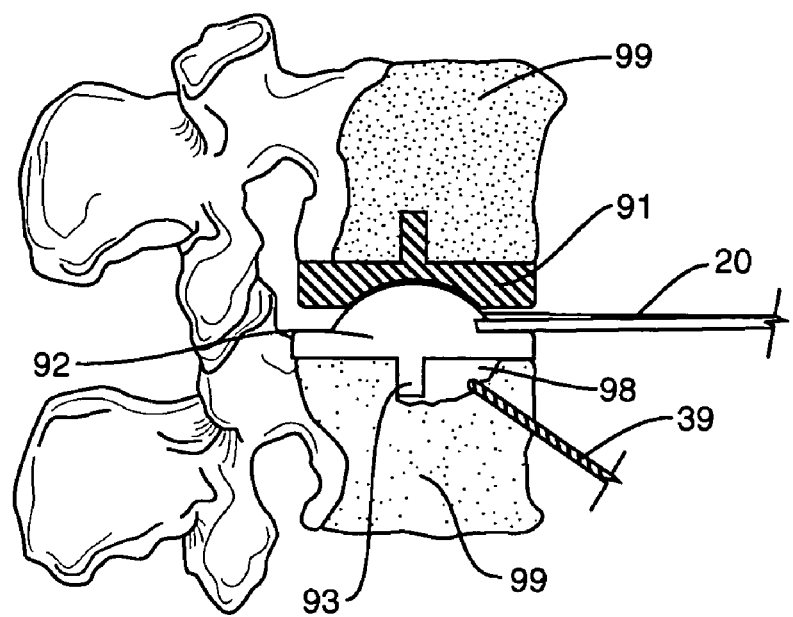
FIG. 8 illustrates a hole forming device being inserted into the vertebral member according to one embodiment of the present invention.
Figure 9:
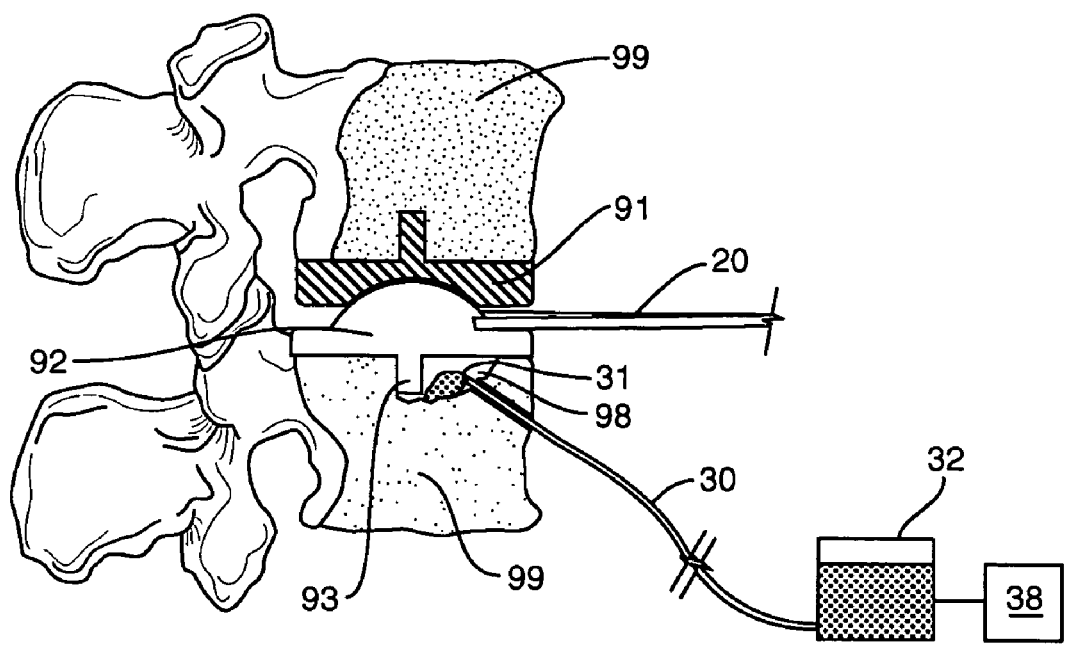
FIG. 9 illustrates a delivery device inserting a material into a gap formed between the vertebral member and the vertebral device according to one embodiment of the present invention.

FIGS. 8 and 9 illustrate another embodiment of filling the gap 98 within the vertebral member 99. In this embodiment, a drill 39 is used to create a passageway into the gap 98.

Once the passageway has been formed, an elongated delivery device 30 is inserted with the tip 31 being positioned within the gap 98. Material 50 stored in a reservoir 32 is forced into the gap 98 by a pump 38. The passageway may be sealed by the material 50, or a separate sealer may be inserted to close the passageway.

In one embodiment, the misaligned vertebral device 90 may remain attached to one or more vertebral members 99. A chisel may be used to detach the device 90. Once detached, the device 90 may be realigned with the positioning tool 20 and reattached with material 50.

In the embodiment illustrated in FIGS. 4-9, only section 92 is realigned while section 91 remains relatively stationary. The non-problematic section 91 may remaining substantially undisturbed while section 92 is being re-positioned and solidified. This protects the non-problematic section 91 from damage that may occur if the section 92 were removed from the body. The section 91 is also protected by maintaining contact between the positioning tool 20 and the section 92 while the material 50 changes towards the second form. The tool 20 prevents the expanding material 50 from moving the section 92 into an incorrect position that may damage section 91.

Various types of intervertebral devices may be re-positioned by the present method. U.S. Patent Application Publication 2005/0043802 entitled "Articular Disc Prosthesis for Lateral Insertion" assigned to SDGI Holdings, Inc. discloses various devices and is herein incorporated by reference in its entirety.

The present invention may be carried out in other specific ways than those herein set forth without departing from the scope and essential characteristics of the invention. The material may further be radio-opaque. In one embodiment, an anterior approach is taken to access the vertebral device 90 and members 99. The present embodiments are, therefore, to be considered in all respects as illustrative and not restrictive, and all changes coming within the meaning and equivalency range of the appended claims are intended to be embraced therein.

What is claimed is:

1. A method of re-positioning a vertebral device that is previously mounted to a vertebral member, the method comprising the steps of:
    accessing the vertebral device and the vertebral member;
    re-aligning the vertebral device to a correct position relative to the vertebral member;
    maintaining the vertebral device in the correct position while delivering a material in a first state to the vertebral member; and
    maintaining the vertebral device in the correct position while allowing the material to change to a second state that is able to maintain the vertebral device in the correct position.

2. The method of claim 1, wherein delivering the material in the first state comprises delivering the material in a liquid or semi-solid form.

3. The method of claim 1, wherein the material changes to a semi-solid or solid in the second state.

4. The method of claim 1, wherein the step of accessing the vertebral device and the vertebral member comprises using an anterior approach.

5. The method of claim 1, further comprising aligning the vertebral device relative to a complimentary second vertebral device on an adjacent vertebral member.

6. The method of claim 5, further comprising preventing the second vertebral device from moving relative to the adjacent vertebral member during the steps of accessing the vertebral device and the vertebral member and re-aligning the vertebral device to the correct position relative to the vertebral member.

7. The method of claim 1, further comprising maintaining the vertebral device in the correct position while allowing the material to change to a solid second state that is able to maintain the vertebral device in the correct position.

8. The method of claim 1, wherein the step of delivering a material in the first state to the vertebral member comprises delivering the material in a liquid form.

9. A method of filling a gap in a vertebral member of a patient that has formed under a vertebral device, the method comprising the steps of:
- accessing the vertebral device and the vertebral member
- accessing the gap that has formed in the vertebral member;
- maintaining the vertebral device within the patient;
- inserting a material in a first state into the gap with a delivery device; and
- using a positioning member to position the vertebral device in a correct position relative to the vertebral member and allowing the material to change into a second state;
- wherein the positioning member positions the vertebral device in the correct position prior to inserting the material into the gap.

10. The method of claim 9, further comprising forming an opening in the vertebral member to access the gap.

11. The method of claim 9, further comprising aligning the vertebral device relative to a complimentary second vertebral device on an adjacent vertebral member.

12. The method of claim 11, further comprising preventing the second vertebral device from moving relative to the adjacent vertebral member during the steps of accessing the vertebral device and the vertebral member and accessing the gap.

13. The method of claim 9, further comprising using an anterior approach to access the vertebral device.

14. The method of claim 9, further comprising allowing the material to change into a solid second state.

15. A method of adjusting a position of a vertebral device comprising the steps of:
- accessing a first section of the vertebral device and a subsided first vertebral member and a second section of the vertebral device and a second vertebral member
- accessing a gap in the subsided first vertebral member;
- inserting a material in a first state into the gap;
- positioning the first section of the vertebral device in a correct position relative to the first vertebral member while the material is in the first state;
- maintaining the first section of the vertebral device in the correct position as the material changes from the first state to a second state; and
- maintaining the second section of the vertebral device while the material is inserted into the gap and while positioning the first section of the vertebral device in the correct position.

16. The method of claim 15, wherein the step of positioning the first section in the correct position comprises positioning a complimentary ball and socket arrangement.

17. The method of claim 15, wherein the step of accessing the first section comprises using an anterior approach.

18. The method of claim 15, further comprising forming a hole in the first vertebral member and accessing the gap.

19. The method of claim 18, further comprising inserting the material through the hole and maintaining an insertion device distanced from the first section.

* * * * *